United States Patent
Rothkopf

(10) Patent No.: US 9,522,175 B2
(45) Date of Patent: *Dec. 20, 2016

(54) METHOD OF ENHANCING DIABETES RESOLUTION

(71) Applicant: Hamilton Scientific, Ltd., Cedar Grove, NJ (US)

(72) Inventor: Michael Rothkopf, North Caldwell, NJ (US)

(73) Assignee: Hamilton Scientific, Ltd., Cedar Grove, NJ (US)

( * ) Notice: Subject to any disclaimer, the term of this patent is extended or adjusted under 35 U.S.C. 154(b) by 4 days.

This patent is subject to a terminal disclaimer.

(21) Appl. No.: 14/243,473

(22) Filed: Apr. 2, 2014

(65) Prior Publication Data
US 2014/0243263 A1    Aug. 28, 2014

Related U.S. Application Data

(63) Continuation of application No. 12/744,099, filed as application No. PCT/US2008/013122 on Nov. 21, 2008, now Pat. No. 8,710,002.

(60) Provisional application No. 61/004,086, filed on Nov. 23, 2007.

(51) Int. Cl.
| | |
|---|---|
| *A61K 38/26* | (2006.01) |
| *A61K 31/40* | (2006.01) |
| *A61K 31/403* | (2006.01) |
| *A61K 31/4985* | (2006.01) |
| *A61K 38/22* | (2006.01) |
| *A61K 31/00* | (2006.01) |

(52) U.S. Cl.
CPC .............. *A61K 38/26* (2013.01); *A61K 31/00* (2013.01); *A61K 31/40* (2013.01); *A61K 31/403* (2013.01); *A61K 31/4985* (2013.01); *A61K 38/22* (2013.01); *A61K 38/2235* (2013.01)

(58) Field of Classification Search
None
See application file for complete search history.

(56) References Cited

U.S. PATENT DOCUMENTS

2007/0167370 A1   7/2007   Gault et al.

FOREIGN PATENT DOCUMENTS

| DK | WO 2006000567 A2 * | 1/2006 | ............. A61K 38/26 |
|---|---|---|---|
| GB | WO 2005082928 A2 * | 9/2005 | ............. C07K 14/575 |
| WO | 2005082928 A2 | 9/2005 | |
| WO | 2006000567 A3 | 6/2006 | |
| WO | WO 2006086769 A2 * | 8/2006 | ............. C07K 14/575 |
| WO | 2006086769 A3 | 11/2006 | |
| WO | 2008/087190 | 7/2008 | |

OTHER PUBLICATIONS

Dixon, Diabetes Care, 25, 2, 2002.*
Drucker, Lancet, 368, 2006.*
Kubota, The Journal of Biological Chemistry, 2003.*
Will Diabetes Go Away, Joslin Diabetes Center, 2015.*
Bose Mousumi et al: Obesity Surgery, 19(2); 217-229 (2009).
Dolan, "Treating Diabetes in the Morbidly Obese by Laparoscopic Gastric Banding", Obesity Surgery, 13, 439-443, 2003.
Drucker, "The Incretin System Glucagon-Like Peptide-1 Receptor Agonists and Dipeptidyl Peptidase-4 Inhibitors in Type 2 Diabetes", Lancet, 368, 2006.
Fetner H et al: Surgery for Obesity and Related Diseases. Else Vieh, NL, 1(6); 589-597 (2005).
Frezza Ermenegildo Eldo: Obesity Surgery 14(7); 999-1005 (2004).
Guidone Caterina et al: Diabetes, 55(7); 2025-2031 (2006).
International Search Report, PCT/US2008/013122, dated Mar. 6, 2009.
Korner et al: Surgery for Obesity and Related Diseases, Elsevier, NL, 3(6); 597-601 (2007).
Korner J et al:Surgery for Obesity and Reiated Diseases, Elsevier, NL, 1(3); 222 (2005).
Kubota, "Ploglitazone Ameliorates Insulin Resistance and Diabetes by Both Adiponectin-dependent and Independent Pathways", The Journal of Biological Chemistry, 2003.
Mingrone et al: NMCD. Nutrition Metabolism and Cardiovascular Diseases, Milan, IT, 18(8); 574-579 (2008).
Morinigo, "GLP-1 and Changes in Glucose Tolerance Following Gastric Bypass Surgery in Morbidly Obese Subjects", Obesity Surgery, 16, 2003.
Rodieux Frederique et al: Obesity (Silver Spring, MD.) 16(2); 298-306 (2008).
Rothkopf Michael M et al: Surgery for Obesity and Related Diseases : Official Journal of the American Society for Bariatric Surgery, 5(1); 128-131 (2000).
Strader et al: Physiology and Behavior. Elsevier Science Ltd., Oxford, GB, 88(3); (2006).

* cited by examiner

*Primary Examiner* — Robert A Wax
*Assistant Examiner* — William Craigo
(74) *Attorney, Agent, or Firm* — Burns & Levinson LLP; Shawn P. Foley

(57) ABSTRACT

Disclosed are compositions and methods for increasing diabetes resolution in a diabetic patient having undergone gastric restrictive surgery, entailing use of active agent that produces an incretin-like effect in the patient.

23 Claims, No Drawings

SEQUENCE LISTING

```
<160> NUMBER OF SEQ ID NOS: 57

<210> SEQ ID NO 1
<211> LENGTH: 37
<212> TYPE: PRT
<213> ORGANISM: Homo sapiens
```

```
<220> FEATURE:
<223> OTHER INFORMATION: N-term H
<220> FEATURE:
<223> OTHER INFORMATION: C-term OH

<400> SEQUENCE: 1

His Asp Glu Phe Glu Arg His Ala Glu Gly Thr Phe Thr Ser Asp Val
1               5                   10                  15

Ser Ser Tyr Leu Glu Gly Gln Ala Ala Lys Glu Phe Ile Ala Trp Leu
            20                  25                  30

Val Lys Gly Arg Gly
            35

<210> SEQ ID NO 2
<211> LENGTH: 30
<212> TYPE: PRT
<213> ORGANISM: Homo sapiens
<220> FEATURE:
<223> OTHER INFORMATION: C-term amide

<400> SEQUENCE: 2

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 3
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 4
<211> LENGTH: 28
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys
            20                  25

<210> SEQ ID NO 5
<211> LENGTH: 29
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

His Ala Glu Gly Thr Phe Thr Ser Asp Val Ser Ser Tyr Leu Glu Gly
1               5                   10                  15
```

Gln Ala Ala Lys Glu Phe Ile Ala Trp Leu Val Lys Gly
            20                  25

<210> SEQ ID NO 6
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 7
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

His Val Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 8
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

His Ala Gln Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 9
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

His Ala Glu Gly Thr Phe Thr Ser Asp Thr Ser Lys Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 10
<211> LENGTH: 31
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 10

His Ala Glu Gly Thr Phe Thr Ser Asp Val Ser Lys Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 11
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term amidated

<400> SEQUENCE: 11

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 12
<211> LENGTH: 39
<212> TYPE: PRT
<213> ORGANISM: Heloderma horridum

<400> SEQUENCE: 12

His Ser Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 13
<211> LENGTH: 39
<212> TYPE: PRT
<213> ORGANISM: Heloderma suspectum

<400> SEQUENCE: 13

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 14
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

His Gly Glu Gly Thr Phe Thr Ser Asp Leu Ser Lys Gln Met Glu Glu
1               5                   10                  15
```

```
Glu Ala Val Arg Leu Phe Ile Glu Trp Leu Lys Asn Gly Gly
            20                  25                  30
```

<210> SEQ ID NO 15
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term amide

<400> SEQUENCE: 15

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly
            20                  25                  30
```

<210> SEQ ID NO 16
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amide

<400> SEQUENCE: 16

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn
            20                  25
```

<210> SEQ ID NO 17
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amide

<400> SEQUENCE: 17

```
His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala Pro Pro Pro Ser
        35
```

<210> SEQ ID NO 18
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amide

<400> SEQUENCE: 18

```
His Gly Glu Gly Thr Phe Thr Ser Asp Leu Ser Lys Gln Leu Glu Glu
1               5                   10                  15
```

```
Glu Ala Val Arg Leu Phe Ile Glu Phe Leu Lys Asn
            20                  25

<210> SEQ ID NO 19
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amide

<400> SEQUENCE: 19

His Gly Glu Gly Thr Phe Thr Ser Asp Leu Ser Lys Gln Leu Glu Glu
1               5                   10                  15

Glu Ala Val Arg Leu Ala Ile Glu Phe Leu Lys Asn
            20                  25

<210> SEQ ID NO 20
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (20)..(20)
<223> OTHER INFORMATION: Lys-(N-epsilon(gamma-Glu(N-alpha-hexadecanoyl)

<400> SEQUENCE: 20

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 21
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Tyr Ala Glu Gly Thr Phe Ile Ser Asp Tyr Ser Ile
1               5                   10

<210> SEQ ID NO 23
```

```
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Tyr Ala Glu Gly Thr Phe Ile Ser Asp Tyr Ser Ile Ala
1               5                   10

<210> SEQ ID NO 24
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Tyr Ala Glu Gly Thr Phe Ile Ser Asp Tyr Ser Ile Ala Met
1               5                   10

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Tyr Ala Glu Gly Thr Phe Ile Ser Asp Tyr Ser Ile Ala Met Asp
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Tyr Ala Glu Gly Thr Phe Ile Ser Asp Tyr Ser Ile Ala Met Asp Lys
1               5                   10                  15

<210> SEQ ID NO 27
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Tyr Ala Glu Gly Thr Phe Ile Ser Asp Tyr Ser Ile Ala Met Asp Lys
1               5                   10                  15

Ile

<210> SEQ ID NO 28
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 28

Tyr Ala Glu Gly Thr Phe Ile Ser Asp Tyr Ser Ile Ala Met Asp Lys
1               5                   10                  15

Ile His

<210> SEQ ID NO 29
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Tyr Ala Glu Gly Thr Phe Ile Ser Asp Tyr Ser Ile Ala Met Asp Lys
1               5                   10                  15

Ile His Gln

<210> SEQ ID NO 30
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Tyr Ala Glu Gly Thr Phe Ile Ser Asp Tyr Ser Ile Ala Met Asp Lys
1               5                   10                  15

Ile His Gln Gln
            20

<210> SEQ ID NO 31
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Tyr Ala Glu Gly Thr Phe Ile Ser Asp Tyr Ser Ile Ala Met Asp Lys
1               5                   10                  15

Ile His Gln Gln Asp
            20

<210> SEQ ID NO 32
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Tyr Ala Glu Gly Thr Phe Ile Ser Asp Tyr Ser Ile Ala Met Asp Lys
1               5                   10                  15

Ile His Gln Gln Asp Phe
            20

<210> SEQ ID NO 33
<211> LENGTH: 23
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 33

Tyr Ala Glu Gly Thr Phe Ile Ser Asp Tyr Ser Ile Ala Met Asp Lys
1               5                   10                  15

Ile His Gln Gln Asp Phe Val
            20

<210> SEQ ID NO 34
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Tyr Ala Glu Gly Thr Phe Ile Ser Asp Tyr Ser Ile Ala Met Asp Lys
1               5                   10                  15

Ile His Gln Gln Asp Phe Val Asn
            20

<210> SEQ ID NO 35
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Tyr Ala Glu Gly Thr Phe Ile Ser Asp Tyr Ser Ile Ala Met Asp Lys
1               5                   10                  15

Ile His Gln Gln Asp Phe Val Asn Trp
            20                  25

<210> SEQ ID NO 36
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Tyr Ala Glu Gly Thr Phe Ile Ser Asp Tyr Ser Ile Ala Met Asp Lys
1               5                   10                  15

Ile His Gln Gln Asp Phe Val Asn Trp Leu
            20                  25

<210> SEQ ID NO 37
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu
            20                  25
```

<210> SEQ ID NO 38
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala
            20                  25

<210> SEQ ID NO 39
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln
            20                  25

<210> SEQ ID NO 40
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys
            20                  25                  30

<210> SEQ ID NO 41
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly
            20                  25                  30

<210> SEQ ID NO 42
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

<210> SEQ ID NO 43
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys

<210> SEQ ID NO 44
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn

<210> SEQ ID NO 45
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp
        35

<210> SEQ ID NO 46
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp
        35

<210> SEQ ID NO 47
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys
        35

<210> SEQ ID NO 48
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His
        35

<210> SEQ ID NO 49
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn
        35

<210> SEQ ID NO 50
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Tyr Ala Glu Gly Thr Phe Ile Ser Asp Tyr Ser Ile Ala Met Asp Lys
1               5                   10                  15

-continued

Ile His Gln Gln Asp Phe Val Asn Trp Leu Leu Ala Gln Lys Gly Lys
            20                  25                  30

Lys Asn Asp Trp Lys His Asn Ile
        35                  40

<210> SEQ ID NO 51
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr
        35                  40

<210> SEQ ID NO 52
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term acetylated

<400> SEQUENCE: 52

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 53
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (37)..(37)
<223> OTHER INFORMATION: Lys-PAL

<400> SEQUENCE: 53

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 54
<211> LENGTH: 42
<212> TYPE: PRT
<213> ORGANISM: Artificial Sequence
<220> FEATURE:

<223> OTHER INFORMATION: Description of Artificial Sequence: Synthetic
      polypeptide
<220> FEATURE:
<223> OTHER INFORMATION: N-term acetylated
<220> FEATURE:
<221> NAME/KEY: MOD_RES
<222> LOCATION: (16)..(16)
<223> OTHER INFORMATION: Lys-PAL

<400> SEQUENCE: 54

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 55
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term acetylated
<220> FEATURE:
<221> NAME/KEY: MOD_RES
<222> LOCATION: (37)..(37)
<223> OTHER INFORMATION: Lys-PAL

<400> SEQUENCE: 55

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 56
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ile Ser Asp Tyr Ser Ile Ala Met Asp Lys Ile His Gln Gln Asp Phe
1               5                   10                  15

Val Asn Trp Leu Leu Ala Gln Lys
            20

<210> SEQ ID NO 57
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: D-Gln

```
<400> SEQUENCE: 57

His Ala Gln Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30
```

METHOD OF ENHANCING DIABETES RESOLUTION

CROSS-REFERENCE RELATED APPLICATIONS

The present application is a continuation of U.S. patent application Ser. No. 12/744,099, filed on Aug. 24, 2010, which application is a national phase entry under 35 U.S.C. §371 of International Application No. PCT/US2008/013122, filed Nov. 21, 2008, published in English, which claims priority from U.S. Provisional Patent Application No. 61/004,086, filed Nov. 23, 2007, all of which are incorporated herein by reference.

SEQUENCE LISTING

The instant application contains a Sequence Listing which has been submitted via EFS-Web and is hereby incorporated by reference in its entirety. Said ASCII copy, created on Feb. 17, 2014, is named MROTH3.3-001_SL.txt, and is 23,735 bytes in size.

BACKGROUND OF THE INVENTION

Obesity is has become a health concern of global proportion. The National Center for Health Statistics (NCHS) estimates that over 120 million Americans are overweight, including about 56% of the adult population. Of these, about 52 million are considered obese, as measured by a body mass index (BMI) of 30% or greater. In Europe, an estimated 77 million people are obese, as measured by the same standard. This problem is not limited to western nations, as many developing countries are reported to have obesity rates over 75% of the adult population.

Type II Diabetes is a significant factor in the obese. Type II diabetes is characterized by a gradual loss of insulin secretion and a progressive reduction in β-cell mass. Insulin resistance increases the demand for insulin. As the β-cell mass declines, the pancreas is unable to sustain the high insulin levels required to maintain normoglycemia.

Weight loss, diet alteration and exercise can improve glycemic control. Beyond these measures, medical therapy of diabetes is intended to control blood sugar within acceptable limits. Patients with diabetes have a wide a number of therapeutic approaches. Medications such as sulfonylureas, biguanides, thiazolidinediones, and alpha-glucosidase inhibitors are available orally. Insulin can be injected or inhaled. Recently a new class of drugs, labeled incretin-mimetics, aimed at enhancing the incretin effect, has been introduced. Many of these drugs, e.g., exenatide, require injection. As effective as they are, however, patients with diabetes can be expected to remain on diabetic medications for their entire lives.

Surgical options exist for obese diabetics, including relatively invasive surgeries such as gastric bypass surgery and duodenal switch surgery, and less invasive surgeries referred to as gastric restriction surgeries. In both gastric bypass and duodenal switch surgery, the capacity of the stomach is significantly reduced and a portion of the small intestine is rerouted. However, the degree of malabsorption is greater in duodenal switch surgery than gastric bypass surgery. Gastric restriction surgeries differ from bypass techniques in that the stomach capacity is reduced but the intestine is left substantially intact.

Diabetes resolution occurs in 48-95% of post-surgical patients, depending on the specific surgery. Thus surgery offers the potential of achieving complete resolution of type II diabetes. This enables patients to stop diabetic medications and glucose self-monitoring entirely.

Gastric bypass procedures (RYGB) incur a great deal of morbidity and create a malabsorptive state in the patient by passing a large portion of the intestines. Diabetes resolution (dR) has been reported to occur in 84% of patients after gastric bypass surgery. Cummings, et al., *Surgery for Obesity and Related Diseases* 3:109-15 (2007).

Gastrointestinal sleeves have been implanted to line the stomach and/or a portion of the small intestines to reduce the absorptive capabilities of the small intestine and/or to reduce the volume in the stomach, by reducing the available volume to the tubular structure of the graft running there through. Although weight loss may be effective while these types of devices are properly functioning, there are complications with anchoring the device within the stomach/GI tract, as the stomach and GI tract function to break down things that enter into them and to move/transport them through. Accordingly, the integrity of the anchoring of the device, as well as the device itself may be compromised over time by the acids and actions of the stomach and GI tract.

A sleeve gastrectomy is an operation in which the left side of the stomach is surgically removed. This results in a much reduced stomach which is substantially tubular and may take on the shape of a banana. This procedure is associated with a high degree of morbidity, as a large portion of the stomach is surgically removed. Additionally, there are risks of complications such as dehiscence of the staple line where the staples are installed to close the surgical incisions where the portion of the stomach was removed. Further, the procedure is not reversible.

In the laparoscopic duodenal switch (also referred to as biliopancreatic diversion or BPD), the size of the stomach is reduced in similar manner to that performed in a sleeve gastrectomy. Additionally, approximately half of the small intestine is bypassed and the stomach is reconnected to the shortened small intestine. This procedure suffers from the same complications as the sleeve gastrectomy, and even greater morbidity is associated with this procedure due to the additional intestinal bypass that needs to be performed. Still further, complications associated with malabsorption may also present themselves. Diabetes resolution has been reported to occur in 95% of patients after duodenal switch surgery (BPD). This diabetes resolution may occur within days after RYGB and BPD, often even before significant weight loss has occurred.

Gastric reduction or restrictive techniques have also been attempted. Unlike bypass procedures, these techniques do not involve reduction of intestinal volume. Such reduction or restrictive techniques include inserting instruments transorally and reducing the volume of the stomach by stapling portions of it together. The LAPBAND™ is a band that, when placed, encircles the fundus-cardia junction and is inflatable to constrict the same. It does not reduce the volume of the stomach, but rather restricts passage of food into the stomach, the theory being that the patient will feel satiety with a much less volume of food than previously. Diabetes resolution has been reported to occur in only 48% of patients after gastric restriction surgery, such as adjustable gastric binding (i.e., the LAPBAND™). Cummings, et al., *Surgery for Obesity and Related Diseases* 3:109-15 (2007).

SUMMARY OF THE INVENTION

An aspect of the present invention is directed to a method for increasing diabetes resolution in a type II diabetic patient having undergone gastric restrictive surgery comprising administering to the patient an agent that produces or causes an incretin-like effect in the patient, in an amount effective to achieve diabetes resolution. In some embodiments, the agent is an incretin hormone such as glucagon-like peptide 1 (GLP-1), gastric inhibitory protein (GIP), or an analog or derivative thereof of GLP-1 or GIP. In some other embodiments, the agent is not an incretin hormone, per se, but acts to increase endogenous incretin hormone activity level, such as by inhibiting degradation of endogenous incretin hormones. In some embodiments, the agent is a DPP IV inhibitor.

The present invention increases diabetic resolution in type II diabetic patients after gastric restriction surgery, thus allowing them to discontinue treatment and medication for diabetes indefinitely or even permanently, and may also improve weight loss outcomes.

DETAILED DESCRIPTION

As used herein, diabetes resolution generally refers to the restoration of normal glucose metabolism, the presence of which can be determined by standard techniques in the art as described and/or referenced herein. The term "administer" (or administered or administering) as used herein includes administration by the patient him/herself.

As used herein, gastric restriction surgery refers to surgeries in which the stomach is altered in a manner that restricts the normal passage of food, leading to a reduction in food intake. This can be accomplished by a reduction in the overall stomach size, a reduction in the gastric capacity or a change in the stomach configuration. Gastric restriction surgery differs from RYGB and BPD because it does not involve a bypass (and thus reduction) of the small intestine. As a result, gastric restriction surgery does not increase the output of gastrointestinal hormones from the K and L cells. Exemplary illustrations of gastric restriction surgeries include LAPBAND™ surgery (adjustable gastric binding) and vertical banded gastroplasty. Other illustrations of gastric restriction surgeries include gastric stapling, gastric partitioning and gastric plication.

Diabetes Mellitus exists in two forms, type I and type II. Type I diabetics have a severe deficiency of insulin production from the β-cells of the pancreatic islets. Their endogenous insulin production is very, very low, and thus inadequate to regulate blood glucose levels. They require injections of insulin to keep their blood glucose normalized and to prevent keto-acidosis. In contrast, type II diabetes is characterized by insulin resistance, which means that additional amounts of insulin must be produced to achieve the same decrease in blood glucose. Insulin resistance generally refers to a condition in which normal amounts of insulin are inadequate to produce a normal insulin response from fat, muscle and liver cells. Insulin resistance in fat cells results in hydrolysis of stored triglycerides, which elevates free fatty acids in the blood plasma. Insulin resistance in muscle reduces glucose uptake, whereas insulin resistance in liver reduces glucose storage, with both effects serving to elevate blood glucose.

Over time, the disease progress to a point where pancreatic cell production of insulin fails to keep up with the body's demand, resulting in an increasingly wide gap between the body's requirements for insulin and its own insulin production. Insulin resistance can be caused by many different kinds of factors, including obesity, medication and genetic factors. Thus, type II diabetics make insulin sufficient to prevent ketoacidosis but not enough to meet the heightened requirements of their insulin-resistant state. Accordingly, treatment of type II diabetes is intended to control three factors, namely glucose delivery, insulin resistance and insulin production.

Without intending to be found by theory, Applicant hypothesizes that the wide difference in diabetes resolution observed between gastric restriction surgery, which has been reported to be about 48%, and the intestinal bypass or diversion procedures, which has been reported to be about 84%, is due to intestinal factors, and that increased gastrointestinal hormone secretion and particularly incretin hormone secretion, creates a metabolic influence in favor of diabetes resolution after RYGB and BPD. The gastric restriction surgery reduces food intake and therefore lowers glucose delivery. The weight loss that typically results from gastric restriction surgery reduces insulin resistance. Therefore, the present inventor hypothesizes that the difference observed in diabetes resolution between gastric restriction surgery and RYGB is most likely due to the lack of increased intestinal hormone secretion after gastric restriction surgery. In other words, both types of surgery achieve control of glucose intake because they cause the patient to ingest less food, albeit in very different ways. However, the increased hormone secretion observed after RGYB corrects the imbalance between insulin resistance and insulin production, and achieves a restoration of normal glucose metabolism and blood levels.

The present invention, therefore, addresses each of these three factors. The invention makes further use of agents with incretin-like activity or which produce or cause an incretin-like effect, which for purposes of the present invention, includes decreased glucose delivery (e.g., appetite reduction, increased satiety and/or slowed gastric emptying), reduced insulin resistance and increased insulin production. Basically, the patient may experience a restoration of normal incretin response to glucose challenge or a supra-normal incretin response to glucose challenge. The combination of this therapeutic intervention not only enhances the effects of gastric restriction surgery by lowering glucose delivery (resulting in lower, e.g., normal, levels of fasting blood or serum glucose) and reducing insulin resistance, but these agents also go further by increasing insulin production. Thus, the combination of gastric restriction surgery and agents with incretin-like activity increase diabetes resolution beyond the 48% reported in the literature as achievable with gastric restriction surgery alone. In some embodiments, the increased diabetes resolution may be as high as 80% or better.

Diabetic patients for whom gastric restriction surgery is recommended tend to be obese. Unless stated otherwise in connection with any specific embodiments disclosed herein, treatment with the agent(s) of the present invention may begin any time after gastric restriction surgery, but usually about 3 months thereafter. By this time, it is more probable that diabetes resolution will have occurred without therapeutic intervention. Timing of the administration is not critical, but is desirably within 1 hour of a meal. Although the time course of the hormone therapy may vary for each patient, the duration of treatment generally ranges from about 1 to about 24 months.

When diabetes resolution occurs after gastric restriction surgery (e.g., LAPBAND™), it usually takes several months and often requires weight loss. Thus, there is a fundamental difference in diabetes resolution in gastric restriction surgery compared to more invasive forms of bariatric surgery to treat obesity. Active agents suitable for use in the present invention include incretin hormones, per se, (including both natural and synthetic versions thereof), analogs, derivatives and mimetics of such hormones, and agents that increase endogenous activity levels of incretin hormones.

Incretin hormones suitable for use in the present methods are recognized to play an important role in food intake, weight loss and glyceric response. These include GLP-1 (glucagon like peptide-1) and GIP (gastric inhibitory peptide, also known as glucose-dependent insulinotropic polypeptide). Together with autonomic nerves they play a vital supporting role to the pancreatic islets in the control of blood glucose homeostasis and nutrient metabolism.

Human GLP-1 is a 37-amino acid peptide (SEQ ID NO:1) originating from preproglucagon, which is synthesized for example, in the L-cells in the distal ileum, in the pancreas and in the brain, and then further processed into shorter peptide(s), e.g., GLP-1 (7-36)amide (SEQ ID NO:2). GLP-1 is normally secreted in response to food intake in particular carbohydrates and lipids stimulate GLP-1 secretion. GLP-1 has been identified as a very potent and efficacious stimulator for insulin release. GLP-1 has been reported to lower plasma glucagon concentrations, slow gastric emptying, stimulate insulin biosynthesis, enhance insulin sensitivity, and enhance the ability of the B-cells to sense and respond to glucose in subjects with impaired glucose tolerance. The insulinotropic effect of GLP-1 in humans has been reported to increase the rate of glucose metabolism partly due to increased insulin levels and partly due to enhanced insulin sensitivity. Other studies have shown that infusions of slightly supra-physiological amounts of GLP-1 significantly enhance satiety and reduce food intake in normal subjects, and that the effect on food intake and satiety is preserved in obese subjects.

As used herein, a "GLP-1 analog" refers to a molecule having a modification including one or more amino acid substitutions, deletions (e.g., fragments), inversions, or additions when compared with GLP-1. A useful GLP-1 analog is GLP-1(7-37), which is represented by the sequence: $NH_2$-His$^7$-Ala-Glu-Gly$^{10}$-Thr-Phe-Thr-Ser-Asp$^{15}$-Val-Ser-Ser-Tyr-Leu$^{20}$-Glu-Gly-Gln-Ala-Ala$^{25}$-Lys-Glu-Phe-Ile-Ala$^{30}$-Trp-Leu-Val-Lys-Gly$^{35}$-Arg-Gly$^{37}$-COOH (SEQ ID NO:3). Other GLP-1 analogs known in the art and that may be useful in the practice of the present invention include, for example, GLP-1(7-34) (SEQ ID NO:4) and GLP-1(7-35) (SEQ ID NO:5), GLP-1(7-36) (SEQ ID NO:6), Val$^8$-GLP-1(7-37) (SEQ ID NO:7), Gln$^9$-GLP-1(7-37) (SEQ ID NO:8), D-Gln$^9$-GLP-1(7-37) (SEQ ID NO: 57), Thr$^{16}$-Lys$^{18}$-GLP-1(7-37) (SEQ ID NO:9), and Lys$^{18}$-GLP-1(7-37) (SEQ ID NO:10), among which include biologically processed versions of full-length GLP-1.

Yet other suitable GLP-1 analogs include exendins (see, e.g., U.S. Patent Application Publication 20060189520), which are peptides that are found in the venom of the Gila-monster, a lizard found in Arizona, and the Mexican Beaded Lizard. Exendin-3 is present in the venom of *Heloderma horridum*, and exendin-4 is present in the venom of *Heloderma suspectum*. The exendins have some sequence similarity to several members of the glucagon-like peptide family, with the highest homology, 53%, being to GLP-1[7-36]NH$_2$ (SEQ ID NO:11) (Goke, et al., *J. Biol. Chem.* 268:19650-55 (1993)). Like GLP-1 (SEQ ID NO:1), exendins have also been reported to inhibit gastric emptying.

Exendins suitable for use in the present invention include exendin-3 (which is represented by the amino acid sequence: His Ser Asp Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala Pro Pro Pro Ser] (SEQ ID NO:12), and exendin-4 (which is represented by the amino acid sequence: His Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala Pro Pro Pro Ser] (SEQ ID NO:13), and other compounds, called exendin agonists, which effectively bind to the receptor at which exendin exerts its action on reducing food intake. Representative exendin agonists include exendin-4 (1-30) (SEQ ID NO:14), exendin-4 (1-30) amide (SEQ ID NO:15), exendin-4 (1-28) amide (SEQ ID NO:16), $^{14}$Leu, $^{25}$Phe exendin-4 amide (SEQ ID NO:17), $^{14}$Leu, $^{25}$Phe exendin-4 (1-28) amide (SEQ ID NO:18), and $^{14}$Leu, $^{22}$Ala, $^{25}$Phe exendin-4 (1-28) amide (SEQ ID NO:19). Exendins and exendin agonists that may be useful in the present invention are disclosed in U.S. Patent Application Publication Nos. 2003/0087821, 2005/0101537 and 2005/0043238.

Exendin compositions useful in the invention may conveniently be provided in the form of formulations suitable for parenteral (including intravenous, intramuscular and subcutaneous) or nasal or oral administration.

As used herein, a "GLP-1 derivative" refers to a molecule having the amino acid sequence of GLP-1 or of a GLP-1 analog, but additionally having at least one chemical modification of one or more of its amino acid side groups, a-carbon atoms, terminal amino group, (e.g., GLP-1 (7-36) amide (SEQ ID NO:2)) or terminal carboxylic acid group. A chemical modification includes adding chemical moieties, creating new bonds, and removing chemical moieties. Modifications at amino acid side groups include acylation of lysine €-amino groups, N-alkylation of arginine, histidine, or lysine, alkylation of glutamic or aspartic carboxylic acid groups, and deamidation of glutamine or asparagine. Modifications of the terminal amino include the des-amino, N-lower alkyl, N-di-lower alkyl, and N-acyl modifications. Modifications of the terminal carboxy group include the amide, lower alkyl amide, dialkyl amide, and lower alkyl ester modifications. A lower alkyl is a $C_1$-$C_4$ alkyl. Furthermore, one or more side groups, or terminal groups, may be protected by protective groups known to the ordinarily-skilled protein chemist. The α-carbon of an amino acid may be mono-methylated or di-methylated. See, e.g., U.S. Patent Application Publication 2004/0018975, and U.S. Pat. Nos. 5,118,666 and 5,545,618. Among the GLP-1 analogs and derivatives taught in U.S. Pat. No. 5,545,618 include those which have amino acid substitutions as positions 7-10 and/or are truncated at the C-terminus and/or contain various other amino acid substitutions in the basic peptide. Analogs and derivatives having D-amino acid substitutions in the 7 and 8 positions and/or N-alkylated or N-acylated amino acids in the position are disclosed therein as being particularly resistant to degradation in vivo. Liraglutide (Arg$^{34}$, Lys$^{26}$ (N$^\epsilon$-(γ-Glu(N$^\alpha$-hexadecanoyl)))-GLP-1(7-37)) (SEQ ID NO:20) is yet another GLP-1 derivative that may be useful in the present invention. Also known as NN2211, liraglutide is a long acting GLP-1 derivative that is obtained by acylation of the GLP-1 molecule, which upon entering the bloodstream, is extensively bound to albumin which protects it from degradation by DPP-IV and reduces renal clearance. See, Elbrond, et al., *Diabetes Care* 25(8):1398-404 (2002); and Madsbad, et al., *Diabetes Care* 27:1335-42 (2004)(and various references cited therein, including Knudsen, et al., *Drugs of the Future* 26:677-85 (2001)). As disclosed in Madsband, liraglutide may be administered via i.v. injection, once-a-day, for about 3 months, or even longer at fixed dosages of from 0.045-0.75 mg, or higher. It is available commercially from Novo Nordisk, Denmark.

GIP is released from intestinal endocrine K-cells into the bloodstream following ingestion of carbohydrate, protein and particularly fat. GIP's major physiological role is now generally believed to be that of an incretin hormone that targets pancreatic islets, and like GLP-1, enhances insulin secretion. (Creutzfeldt, W., *Exp. Clin. Endocrinol. Diabetes* 109:S288-S303 (2001)). GIP also helps reduce postprandial hyperglycemia. Id. GIP acts through binding to specific G-protein coupled GIP receptors located on pancreatic beta-cells (Wheeler, et al., *Endocrinology* 136:4629-39 (1995)).

Naturally occurring GIP (also referred to as native GIP) is a 42-amino acid peptide hormone, having the (human) sequence Tyr Ala Glu Gly Thr Phe Ile Ser Asp Tyr Ser Ile Ala Met Asp Lys Ile His Gln Gln Asp Phe Val Asn Trp Leu Leu Ala Gln Lys Gly Lys Lys Asn Asp Trp Lys His Asn Ile Thr Gln (SEQ ID NO:21). GIP antagonists that are relatively resistant to degradation by DPP IV are also useful in the present invention. Such antagonists, also referred to as peptide analogues of GIP(1-42), include GIP(1-12) (SEQ ID NO:22), GIP(1-13) (SEQ ID NO:23), GIP(1-14) (SEQ ID NO:24), GIP(1-15) (SEQ ID NO:25), GIP(1-16) (SEQ ID NO:26), GIP(1-17) (SEQ ID NO:27), GIP(1-18) (SEQ ID NO:28), GIP(1-19) (SEQ ID NO:29), GIP(1-20) (SEQ ID NO:30), GIP(1-21) (SEQ ID NO:31), GIP(1-22) (SEQ ID NO:32), GIP(1-23) (SEQ ID NO:33), GIP(1-24) (SEQ ID NO:34), GIP(1-25) (SEQ ID NO:35), GIP(1-26) (SEQ ID NO:36), GIP(1-27) (SEQ ID NO:37), GIP(1-28) (SEQ ID NO:38), GIP(1-29) (SEQ ID NO:39), GIP(1-30) (SEQ ID NO:40), GIP(1-31) (SEQ ID NO:41), GIP(1-32) (SEQ ID NO:42), GIP(1-33) (SEQ ID NO:43), GIP(1-34) (SEQ ID NO:44), GIP(1-35) (SEQ ID NO:45), GIP(1-36) (SEQ ID NO:46), GIP(1-37) (SEQ ID NO:47), GIP(1-38) (SEQ ID NO:48), GIP(1-39) (SEQ ID NO:49), GIP(1-40) (SEQ ID NO:50), GIP(1-41) (SEQ ID NO:51) and GIP(1-42) (SEQ ID NO:21), where the base peptide possesses one or more of the following modifications: (1) an amino acid substitution at $Glu^3$, e.g., proline, hydroxyproline, lysine, tyrosine, phenylalanine or tryptophan; (2) a modification by fatty acid addition e.g., a C-8, C-10, C-12, C-14, C-16, C-18 or a C-20 palmitate (PAL) group to an epsilon amino group of at least one lysine residue e.g., $Lys^{16}$ or $Lys^{37}$, which have been reported to circumvent the problem of renal filtration; and (3) a modification by N-terminal acetylation. See, e.g., U.S. Patent Application Publication 2007/0167370. Although literature categorizes all three categories as GIP-1 antagonists or analogs, consistent with usage of terminology in the present invention, the modified GIP-1 proteins in the first category are referred to as GIP-1 analogs, and the modified GIP proteins in the latter two categories are referred to as GIP-1 derivatives. Thus, specific representative GIP analogs and derivatives include N-AcGIP (1-42) (SEQ ID NO:52), GIP(1-42) ($Lys^{37}$PAL) (SEQ ID NO:53), N-AcGIP(1-42) ($Lys^{16}$PAL) (SEQ ID NO:54) and N-AcGIP(1-42) ($Lys^{37}$PAL) (SEQ ID NO:55). Further analogs are disclosed in U.S. Patent Application Publication Nos. 20020151495, 20030232761, and 2007/0167363 (e.g., GIP (7-30) (SEQ ID NO:56)).

Administration of GIP or its analogs or derivatives of the present invention used in the pharmaceutical composition or to practice the method of the present invention can be carried out in a variety of conventional ways, such as by oral ingestion, inhalation, topical application or cutaneous, subcutaneous, intraperitoneal, parenteral or intravenous injection.

Dipeptidyl peptidase IV (DPP-IV) inhibitors refer to compounds that inhibit activity of DPP-IV, a membrane-associated amino peptidase of 766 amino acids that acts preferentially on substrates with an amino-terminal proline or alanine at position 2, such as GLP-1, GLP-2, and GIP. Inhibitors of DPP-IV have been shown to increase circulating levels of GLP-1 and GIP; thus, they may show an enhanced effect on diabetes resolution for purposes of the present invention. Suitable DPP-IV inhibitors include sitagliptin ((R)-3-Amino-1-(3-trifluoromethyl-5,6-dihydro-8H-[1,2,4]triazolo[4,3-a]-pyrazin-7-yl)-4-(2,4,5-trifluoro-phenyl)-butan-1-one, described in WO 03/004498, and commercially available from Merck & Co.), vildagliptin (pyrrolidine, 1-[(3-hydroxy-1-adamantyl)amino]acetyl-2cyano-, (S), or (S)-1-2-((5S,7S)-3-Hydroxy-adamantan-1-ylamino)-acetyl]-pyrrolidine-2-carbonitrile, described in WO 00/034241, and commercially available from Novartis), and saxagliptin ((1S,3S,5S)-2-[(S)-2-amino-2-(3-hydroxy-adamantan-1-yl)-acetyl]-2-aza-bicyclo[3.1.0]hexane-3-carbonitrile, described in WO 01/68603). In addition to these compounds, other DPP IV inhibitors that may be useful in practicing the present invention are described in U.S. Patent Application Publication 2007/0098781 (and publications referenced therein). DPP-IV inhibitors are typically administered orally.

The agents of the present invention may be prepared in accordance with standard techniques, disclosed for example in the literature cited herein, including (particularly with respect to the peptide-based agents) solid-phase synthetic chemistry and recombinant DNA technology (with respect to the amino acid portion of the product), coupled with subsequent chemical modification, enzymatic modification and combinations thereof.

The agents may be administered in the form of pharmaceutically acceptable salts, e.g., acid-addition salts and basic-addition salts. Acids commonly employed to form acid addition salts are inorganic acids such as hydrochloric acid, hydrobromic acid, hydroiodic acid, sulfuric acid, phosphoric acid, and the like, and organic acids such, as p-toluenesulfonic acid, methanesulfonic acid, oxalic acid, p-bromophenyl-sulfonic acid, carbonic acid, succinic acid, citric acid, benzoic acid, acetic acid, and the like. Examples of such salts include the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycolate, tartrate, methanesulfonate, propanesulfonate, naphthalene-1-sulfonate, naphthalene-2-sulfonate, mandelate, and the like. Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, and the like. Unless already present in a derivative of the agent, the agents may also be administered in the form of a pharmaceutically lower alkyl ester or amide.

Administration of the agents of the present invention may be via any route known to be safe and effective by the physician of ordinary skill in the art. When a therapeutically effective amount of the composition of the present invention is administered orally, the composition of the present invention will be in the form of a tablet, capsule, powder, solution or elixir. When administered in tablet form, the pharmaceutical composition of the invention may additionally contain a solid carrier such as a gelatin or an adjuvant. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. Controlled release preparations may be achieved by the use of polymers to complex or absorb the active compound used in the present invention. Extended duration may be obtained by selecting appropriate macromolecules, for example, polyesters, polyamino acids, polyvinylpyrrolidone, ethylene/vinyl acetate, methylcellulose, carboxymethylcellulose, or protamine sulfate, and by selecting the concentration of macromolecules, as well as the methods of incorporation, in order to prolong release. Such teachings are known to those of skill in the art and disclosed, e.g., in *Remington's Pharmaceutical Sciences*, 1980.

In other embodiments, delivery of the active agent is via peripheral, parenteral administration, which as used herein refers to the injection of a dosage form into the body by a sterile syringe or some other mechanical device such as an infusion pump. Suitable peripheral parenteral routes include intravenous, intramuscular, subcutaneous, and intraperitoneal routes of administration. Formulations suitable for parenteral administration include aqueous and non-aqueous sterile injection solutions (e.g., a vehicle such as Sodium Chloride Injection, Ringer's Injection, Dextrose Injection, Dextrose and Sodium Chloride Injection or Lactated Ringer's Injection, which may contain anti-oxidants, buffers, bacteriostats and solutes which render the formulation isotonic with the blood of the intended recipient; and aqueous and non-aqueous sterile suspensions which may include suspending agents and thickening agents, preservatives, buffers, antioxidants, or other additives (e.g., wetting or emulsifying agents) known to those of skill in the art. The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

Agents of the present invention may also be administered topically or nasally.

The amount of agents of the present invention will depend upon the nature and severity of the diabetic condition being treated, the nature of prior treatments which the patient has undergone, and on a variety of other factors, including the type of injury, the age, weight, sex, medical condition of the patient. Ultimately, the attending physician will decide the amount of the agent with which to treat each individual patient. Initially, the attending physician may administer low doses of agent and observe the patient's response. Larger doses of agent may be administered until the optimal therapeutic effect is obtained for the patient, and at that point the dosage is not increased further.

Guidance on methods of determining dosages can be found in standard references, for example, Spilker, *Guide to Clinical Studies and Developing Protocols*, Raven Press Books, Ltd., New York, 1984, pp. 7-13 and 54-60; Spilker, *Guide to Clinical Trials*, Raven Press, Ltd., New York, 1991, pp. 93-101; Craig et al., *Modern Pharmacology*, 2d ed., Little Brown and Co., Boston, 1986, pp. 127-133; Speight, *Avery's Drug Treatment Principles and Practices of Clinical Pharmacology and Therapeutics*, 3d ed., Williams and Wilkins, Baltimore, 1987, pp. 50-56; Tallarida et al., *Principles in General Pharmacology*, Springer-Verlag, New York, 1998, pp. 18-20; and Olson, *Clinical Pharmacology Made Ridiculously Simple*, MedMaster, Inc., Miami, 1993, pp. 1-5.

More specifically, for example, A typical dosage range for GLP-1 and analogs and derivatives is about 1 pg/kg-1 mg/kg body weight, although these are approximations depending upon a large number of factors including the potency of the analog, its circulating half-life, the individual characteristics of the subject, and the like. Optimization of administration of insulin for diabetic treatment of individuals is well established, and similar optimization protocols are employed here. For purposes of illustration, in some embodiments, amounts of native GLP-1 range from about 0.03 to about 100 nmol/kg, and GLP-1 is administered via injection or by subcutaneous infusion, e.g., at a dose of 4.8 pmol/kg/min using a portable pump.

Doses of exendins for achieving enhancement of diabetes resolution will typically be in the range of about 10 to 30 µg to about 5 mg/day, preferably about 10 to 30 µg to about 2 mg/day and more preferably about 10 to 100 µg to about 1 mg/day, most preferably about 30 µg to about 500 µg/day, for a 70 kg patient, administered in a single or divided doses. By way of illustration, exendin-4 (commercially available from Amylin and Eli Lilly & Co. under the name BYETTA, and as a generic version known as exenatide) is usually administered subcutaneously, in amounts ranging from about 5 to about 30 micrograms per day, and in some embodiments, is administered starting with 10 micrograms per day in two divided doses, and then increased e.g., after about one month, as required e.g., to 20 micrograms per day, and even up to about 30 micrograms or more per day, for at least e.g., 1, 2, 3, 4, 5, 6, 7, 8, 9, 10, 11, 12 or more additional months. Thus, in some embodiments, the individual formulation, e.g., for oral administration, contains about 5, 10 or 15 micrograms (corresponding to a divided daily total dose of 10, 20 or 30 micrograms).

For example, in some embodiments, GIP (1-42) (SEQ ID NO:21) is administered by subcutaneous infusion in dosages ranging from about 0.1 to about 10 pmol/kg/min (e.g., about (1-4 pmol/kg/min) or by bolus injection ranging from about 6.25 to about 25 nmol/kg/day. By way of additional example, in some other embodiments, GIP or GIP analogue is administered subcutaneously in dosages ranging from about 6.25 to about 25 nmol/kg/day, wherein if required, the dosage is increased over the treatment period or a portion thereof, e.g., with initial dosages of about 6.25 nmol/kg/day and a maximum of about 25 nmol/kg/day.

DPP IV inhibitors may be administered at an initial dosage of about 100 mg/day. The dosage may be increased if necessary, with a maximum of about 200 mg/day.

Individual patients will have varying responses to treatments with the gastrointestinal hormones described herein. Clinicians skilled in the art will therefore appreciate that for some patients a combination of the therapies will be more effective than any single therapy alone. Patient clinical and/or biochemical characteristics will guide clinicians in choosing combination therapies to achieve diabetes resolution after gastric restriction surgery. Representative combinations of hormones suitable for use in the present invention may include GIP and GLP-1; and GLP-1 and the DPP IV inhibitor sitagliptin.

Diabetic resolution is judged to have occurred when evidence of normal glucose metabolism is present. This includes, but is not limited to: a fasting glucose below about 125 mg/dL, hbA1c below about 7%, fasting insulin above about 7 microunits/ml, fasting c-peptide above about 0.4 ng/ml, and a 2 hour post glucose loading c-peptide above about 2.0 ng/ml. These values may have an uncertainty value of +/−5%.

Once diabetes resolution has occurred, therapy with GLP-1 or analog is discontinued. At this point, the patient is encouraged to continue home fasting and glucose monitoring for 30 days. If the fasting glucose remains below 125, the patient is considered to be non-diabetic. Home glucose monitoring is then discontinued.

Embodiments of the present invention are now described in connection with the following non-limiting examples.

EXAMPLES

The first example is that of a 63 year old, morbidly obese Caucasian male, with type II diabetes for many years. He weighed 331 pounds and had a body mass index of 44. His preoperative medications included repaglinide and metformin. The patient underwent laproscopic gastric restriction surgery. He was placed on a low calorie, high protein, bariatric diet and encouraged to exercise regularly. However, he remained diabetic despite experiencing a 56-pound weight loss. He was started on exenatide and instructed to discontinue his prior diabetic medications. The initial dosage was 10 mcg daily which was advanced to 20 mcg after one month.

He lost an additional 44 pounds during the 13 months on exenatide. This was much more than would have been expected by gastric restriction surgery alone. His fasting glucose was 95 with post prandial glucoses below 150. He was instructed to discontinue exenatide. He continued home fasting glucose monitoring for 30 days. The fasting glucose remained below 125. Home glucose monitoring was then discontinued. He continued routine follow care. His diabetes was considered to have been resolved.

The second example is that of a 51-year old, morbidly obese Caucasian male, with type II diabetes for many years. He weighed 348 pounds and had a body mass index of 50. His preoperative medications included metformin. The patient underwent laparoscopic gastric restriction surgery. He was placed on a low calorie, high protein, bariatric diet and encouraged to exercise regularly. However, after 3 months he had experienced only a modest weight loss of 15 pounds and remained diabetic. He was started on exenatide and instructed to discontinue his prior diabetic medications. The initial dosage was 10 mcg daily which was advanced to 20 mcg after one month.

He lost an additional 51 pounds during the 7 months on exenatide. This was much more than had been expected by gastric restriction surgery alone. His fasting glucose was 95 with post prandial glucoses below 150. He was instructed to discontinue exenatide. He continued home fasting glucose monitoring for 30 days. The fasting glucose remained below 125. Home glucose monitoring was then discontinued. He continued routine follow care. His diabetes was considered to have been resolved.

The third example is that of a 71-year old, morbidly obese Caucasian female, with type II diabetes for many years. She weighed 315 pounds and had a body mass index of 55.8. Her preoperative medications included glimipride, nateglinide and metformin. The patient underwent laparoscopic gastric restriction surgery. She was placed on a low calorie, high protein, bariatric diet and encouraged to exercise regularly. However, after 3 months she had experienced only a modest weight loss of 21 pounds and remained diabetic. She was started on exenatide. She discontinued her prior diabetic medications after one month. The initial dosage of exenatide was 10 mcg daily which was advanced to 20 mcg after one month.

She lost an additional 53 pounds during the 7 months on exenatide. This was much more than the amount that would have been expected by gastric restriction surgery alone. Her fasting glucose and post prandial glucoses were below 110. Her HbA1C was <6%. Her diabetes was considered to have been resolved.

The fourth example is that of a 55-year old, morbidly obese Caucasian female, with recently diagnosed with type II diabetes. She weighed 252 pounds and had a body mass index of 40. She was not on preoperative diabetic medications. The patient underwent laparoscopic gastric restriction surgery. She was placed on a low calorie, high protein, bariatric diet and encouraged to exercise regularly. She was started on exenatide postoperatively. The initial dosage was 10 mcg daily which was advanced to 20 mcg after one month.

She lost 96 pounds during the 7 months on exenatide. This was much more than the amount that would have been expected by gastric restriction surgery alone. Her fasting glucose and post prandial glucoses were below 110. Her HbA1C was <6%. Her diabetes was considered to have been resolved.

INDUSTRIAL APPLICABILITY

The present invention has applicability in clinical medicine and therapeutics, and more specifically for example in the treatment of obese diabetics.

All patent and non-patent publications cited in this specification are indicative of the level of skill of those skilled in the art to which this invention pertains. All these publications and patent applications are herein incorporated by reference to the same extent as if each individual publication or patent application was specifically and individually indicated to be incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for treating a type II diabetic patient having undergone gastric restrictive surgery that does not involve a bypass to achieve diabetes resolution, comprising administering to the patient an agent that produces an incretin-like effect in the patient in an amount effective to achieve diabetes resolution, wherein the agent comprises a DPP-IV inhibitor, and wherein said treating increases likelihood of achieving the diabetes resolution relative to a patient having undergone the gastric restrictive surgery but who has not had said treating.

2. The method of claim 1, wherein the DPP-IV inhibitor is sitagliptin.

3. The method of claim 1, wherein the DPP-IV inhibitor is vildagliptin.

4. The method of claim 1, wherein the DPP-IV inhibitor is saxagliptin.

5. The method of claim 1, wherein the amount of the DPP-IV inhibitor is about 100 mg/day.

6. The method of claim 1, wherein the amount of the DPP-IV inhibitor is about 300 mg/day.

7. The method of claim 1, further comprising: administering at least one additional agents.

8. The method of claim 7, wherein the at least one additional agent comprises glucagon-like peptide 1 (GLP-1), or an analog or derivative of GLP-1.

9. The method of claim 8, wherein the at least one additional agent comprises exendin-4.

10. The method of claim 9, wherein exendin-4 is administered in a daily dosage of about 5 to about 30 micrograms.

11. The method of claim 9, wherein exendin-4 is administered in a daily dosage of about 10 micrograms.

12. The method of claim 10, wherein said daily dosage comprises two divided doses.

13. The method of claim 12, wherein said daily dosage comprises about 20 micrograms.

14. The method of claim 9, wherein the patient is administered exendin-4 in a first daily dosage of about 10 micrograms, wherein said first daily dosage is administered for about 1 month, and wherein said patient is then administered exendin-4 in a second daily dosage of about 20 micrograms.

15. The method of claim 14, wherein said second daily dosage is continued for at least one month.

16. The method of claim 15, wherein said second daily dosage is continued for at least 6 months.

17. The method of claim 15, wherein said second daily dosage is continued for at least 12 months.

18. The method of claim 7, wherein the at least one additional agent comprises gastric inhibitory peptide (GIP) or an analog or derivative thereof.

19. The method of claim 18, wherein the analog of GIP comprises N-AcGIP (1-42), GIP(1-42)(Lys$^{37}$PAL), N-Ac-GIP (1-42)(Lys$^{16}$PAL) or N-AcGIP(1-42)(Lys$^{37}$PAL).

20. The method of claim 7, wherein the at least one additional agent comprises GIP-1 or an analog or derivative thereof, and GLP-1 or an analog or derivative thereof.

21. The method of claim 7, wherein the at least one additional agent comprises GLP-1 or an analog or derivative thereof, wherein the DPP-IV inhibitor is sitagliptin.

22. The method of claim 1, wherein the gastric restriction surgery undergone by the patient comprises adjustable gastric banding, vertical banded gastroplasty, gastric stapling, gastric partitioning, or gastric pliation.

23. The method of claim 1, wherein the DPP-IV inhibitor is administered orally.

* * * * *